United States Patent [19]

Eckhardt et al.

[11] 4,207,338
[45] Jun. 10, 1980

[54] MICROBICIDAL COMPOSITION

[75] Inventors: Wolfgang Eckhardt, Lörrach, Fed. Rep. of Germany; Walter Kunz, Oberwil; Adolf Hubele, Magden, both of Switzerland

[73] Assignee: Ciba-Geigy Corporation, Ardsley, N.Y.

[21] Appl. No.: 39,011

[22] Filed: May 11, 1979

[30] Foreign Application Priority Data

May 19, 1978 [CH] Switzerland .......................... 5461/78

[51] Int. Cl.² .................. A61K 31/24; C07C 101/447
[52] U.S. Cl. ...................................... 424/309; 560/21; 560/34
[58] Field of Search ................ 560/34, 21; 424/309

[56] References Cited

U.S. PATENT DOCUMENTS

| | | | |
|---|---|---|---|
| 3,780,095 | 12/1973 | Klemm et al. | 560/43 |
| 4,093,738 | 6/1978 | Hubele | 424/309 |
| 4,151,299 | 4/1979 | Hubele | 560/43 |

*Primary Examiner*—Bernard Helfin
*Assistant Examiner*—G. T. Breitenstein
*Attorney, Agent, or Firm*—Harry Falber

[57] ABSTRACT

Hydrazino-acetanilide derivatives of the formula I

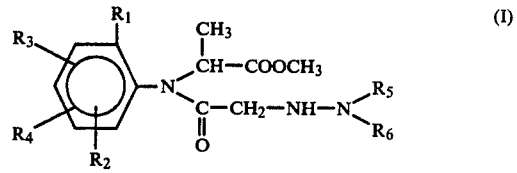

wherein
  $R_1$ is $C_1-C_4$ alkyl, $C_1-C_4$ alkoxy or halogen,
  $R_2$ is $C_1-C_3$ alkyl, $C_1-C_4$ alkoxy or halogen,
  $R_3$ is hydrogen, $C_1-C_3$ alkyl or halogen,
  $R_4$ is hydrogen or methyl, with the total number of C atoms of the substituents $R_1$, $R_2$, $R_3$ and $R_4$ in the phenyl ring not exceeding 6,
  $R_5$ is $C_1-C_5$ alkyl which is unsubstituted or substituted by halogen, or it is phenyl which is unsubstituted or substituted by methyl, nitro and/or halogen, or it is the benzyl group, and
  $R_6$ is hydrogen or $C_1-C_5$ alkyl, possess valuable microbicidal properties, and contained in appropriate compositions these derivatives can be used in particular for combating phytopathogenic fungi.

10 Claims, No Drawings

MICROBICIDAL COMPOSITION

The present invention relates to compounds of the formula I, and to salts thereof which are tolerated by plants,

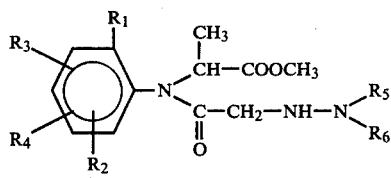

wherein
- $R_1$ is $C_1$-$C_4$ alkyl, $C_1$-$C_4$ alkoxy or halogen,
- $R_2$ is $C_1$-$C_3$ alkyl, $C_1$-$C_4$ alkoxy or halogen,
- $R_3$ is hydrogen, $C_1$-$C_3$ alkyl or halogen,
- $R_4$ is hydrogen or methyl, with the total number of C atoms of the substituents $R_1$, $R_2$, $R_3$ and $R_4$ in the phenyl ring not exceeding 6,
- $R_5$ is $C_1$-$C_5$ alkyl which is unsubstituted or substituted by halogen, or it is phenyl which is unsubstituted or substituted by methyl, nitro and/or halogen, or it is the benzyl group, and
- $R_6$ is hydrogen or $C_1$-$C_5$ alkyl.

By alkyl or by alkyl moiety of an alkoxy group are meant, depending on the given number of carbon atoms, the following groups: methyl, ethyl, propyl, butyl or pentyl, and also their isomers, for example iso-propyl, iso-, sec- or tert-butyl, 1-methylbutyl, 1-ethylpropyl, and so forth.

The term 'halogen' embraces fluorine, chlorine, bromine and iodine.

By salts which are tolerated by plants are meant those of the following inorganic or organic acids. Examples of inorganic acids are hydrochloric acid, hydrobromic acid, hydriodic acid, sulfuric acid, phosphoric acid, phosphorous acid and nitric acid. Examples of organic acids are acetic acid, trichloroacetic acid, oxalic acid, succinic acid, maleic acid, lactic acid, glycolic acid, aconitic acid, citric acid, benzoic acid, benzenesulfonic acid and methanesulfonic acid. These are given purely as examples and in no way do they constitute any limitation.

The invention relates also to microbicidal compositions which contain, as at least one active ingredient, a compound of the formula I. The invention relates also to a process for combating fungi and bacteria, which process involves the use of compounds of the formula I. ω-Aminoacylanilines with halogen atoms, alkyl or alkoxy groups in the ortho-positions of the phenyl ring are already known. Thus, for example, Xylocain (=2-diethylaminoaceto-2',6'-dimethylanilide) is available commercially as a local anaesthetic [Merck Index, 8th Edition, page 618, (Merck Co. Inc.)].

In the German Offenlegungsschrift No. 2,400,540 are suggested primary amino-acyl-2',6'-di-(subst.)-anilides as therapeutic compounds having anti-arrhythmic properties. There is no reference made however to microbicidal action against phytopathogenic fungi. The nearest comparable substances, designated as preferred substances in this publication, such as N-(2-aminopropionyl)-N-ethyl-2',6'-dimethylaniline, N-aminoacetyl-2,6-diethylaniline, N-3-aminopropionyl-2',4',6'-trimethylaniline, N-aminoacetyl-2',6'-diethoxyaniline or N-(2-aminopropionyl)-2',6'-dichloroaniline, are ineffective against pathogens of plant diseases.

It has now been found that, surprisingly, compounds having the structure of the formula I exhibit a very favourable microbicidal spectrum for practical requirements for the protection of cultivated plants. Cultivated plants within the scope of the present invention are for example: cereals, maize, rice, vegetables, sugar beet, soya bean, groundnuts, fruit trees or ornamental plants, especially however grape vines, hops, cucurbitaceae (cucumbers, pumpkins, melons), solanaceae, such as potatoes, tobacco and tomatoes, and also bananas, cocoa and natural rubber plants.

Fungi occurring on plants or on parts of plants (fruit, blossom, foliage, stalks, tubers or roots) of the said crops and of related cultivated crops can be inhibited or destroyed with the active substances of the formula I, and also parts of plants subsequently growing remain preserved from such fungi. The active substances are effective against the phytopathogenic fungi belonging to the following classes: Ascomycetes (for example Erysiphaceae); Basidiomycetes, such as in particular rust fungi; Fungi imperfecti (for example Moniliales); and especially against the Oomycetes belonging to the Phycomycetes class, such as Phytophthora, Peronospora, Pseudoperonospora, Pythium or Plasmopara. Furthermore, the compounds of the formula I have a systemic action. They can also be used as dressing agents for the treatment of seed (fruits, tubers and grain) and plant cuttings to protect them from fungus infections, and also against phytopathogenic fungi occurring in the soil.

One of the preferred subgroups is formed by those compounds of the formula I in which $R_1$ is methyl, $R_2$ is in the ortho-position with respect to the amino group and is methyl, methoxy or chlorine, $R_3$ is hydrogen, methyl or chlorine, and $R_4$ is hydrogen or methyl. This group is to be called compound group Ia.

One of the particularly preferred subgroups within the compound group Ia embraces those compounds in which $R_5$ is $C_1$-$C_3$ alkyl, and $R_6$ is hydrogen or $C_1$-$C_3$ alkyl. This group is to be denoted as compound group Ib.

Even at high concentrations, compounds of the formula I are in general well tolerated by cultivated plants.

According to further subject matter of the present invention, the compounds of the formula I are obtained (A) by acylation of a compound of the formula II

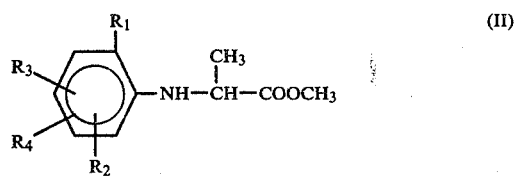

with a carboxylic acid of the formula III

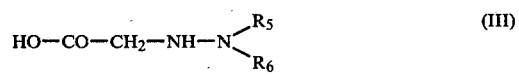

or with its ester, acid anhydride or acid halide; or (B) by initial appropriate monohaloacetylation of a compound of the formula II to an intermediate of the formula IV

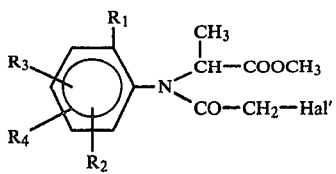

(IV)

and further reaction with the hydrazino derivative of the formula V $$H_2N-N(R_5)(R_6) \quad (V).$$

In the case of the process variant A, it is possible to produce from the hydrazinoacetic acid of the formula III the acid halide also intermediately by passing for example thionyl chloride into the reaction solution.

In the formulae II, III, IV and V, the symbols $R_1$ to $R_6$ have the meanings given for the formula I, whilst Hal' is a halogen atom, preferably chlorine or bromine.

A compound of the formula I is obtained as a hydrohalide when it is produced, according to the process variant B or according to the process variant A, with the use of the acid halide of a compound of the formula III. With mild bases it is possible to obtain from the hydrohalide, at room temperature or at slightly elevated temperature, the free hydrazino compound. Suitable for this purpose are for example alkali carbonates.

The reactions A and B can be performed in the presence or absence of solvents or diluents which are inert to the reactants. The following are for example suitable: aliphatic hydrocarbons such as benzene, toluene, xylenes or petroleum ether; halogenated hydrocarbons such as dialkyl ether, dioxane or tetrahydrofuran; nitriles such as acetonitrile; N,N-dialkylated amides such as dimethylformamide; dimethyl sulfoxide or ketones such as methyl ethyl ketone; and mixtures of solvents of this kind.

The reaction temperatures are between 0° and 180° C., preferably between 20° and 80° C. The use of acid-binding agents and condensation agents is advantageous in some cases. Suitable as such are tertiary amines such as trialkylamines (for example triethylamine), pyridine and pyridine bases, or inorganic bases, such as the oxides and hydroxides, hydrogen carbonates and carbonates of alkali metals and alkaline-earth metals, and also sodium acetate. It is also possible to use as acid-binding agent in the two process variants one of the basic starting products II, III or V and also the formed end product I.

The production process A starting with compounds of the formula II can be performed also without acid-binding agents, and it is then advisable in some cases to pass nitrogen through in order to expel the hydrogen halide formed. In other cases, an addition of dimethylformamide as a reaction catalyst is very advantageous. Details concerning the production of intermediates of the formula II can be gathered from a study of the methods given in general for the production of anilinoalkanoic acid esters in U.S. Pat. No. 3,598,859, and of N-alkoxyalkylanilines in G.B. Pat. No. 1,438,311.

The uncomplicated production of compounds of the formula I using the aforementioned process variants A and B is very surprising, since either a cyclisation of the strongly basic hydrazino side chain with the propionic acid ester side chain, in the sense of an intramolecular amidation, or a hydrazide formation of the ester group would have been the result to be anticipated.

The compounds of the formula I contain in the ester side chain as asymmetrical carbon atom (*), and can be split in the customary manner into optical antipodes. In this respect, the enantiomeric D form has the stronger microbicidal action. Accordingly, within the scope of the invention, preferred compounds are those compounds, their compositions, and the use thereof, which relate to the D configuration of the formula I.

The pure optical D antipodes are obtained for example by producing the racemic compound of the formula VI

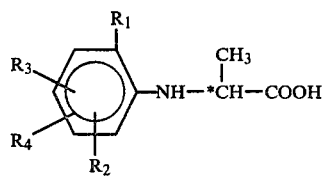

(VI)

wherein $R_1$, $R_2$, $R_3$ and $R_4$ have the meanings given for the formula I, and then reacting it, in a manner known per se, with a nitrogen-containing, optically active base to give the corresponding salt. By fractional crystallisation of the salt and subsequent liberation of the acid of the formula VI, which is enriched with the optical D antipode, and optionally a repeat (also several repeats) of the salt formation, crystallisation and liberation of the α-anilinopropionic acid of the formula VI, there is obtained stepwise the pure D form. From this it is then possible to produce, if desired, in the usual manner, for example in the presence of HCl or $H_2SO_4$, with methanol the optical D configuration of the methyl ester on which the formula II is based.

A suitable optionally active organic base is for example α-phenylethylamine.

Provided that no specific synthesis for isolation of the pure isomers is performed, a product of the formula I is normally obtained as a mixture of these possible isomers.

The Examples which follow serve to further illustrate the invention without limiting its scope. The temperature values are given in degrees Centigrade. Except where otherwise stated, the racemic mixture is to be understood in every case where there is mention of an active substance of the formula I.

EXAMPLE 1

Production of (Compound No. 1.1)

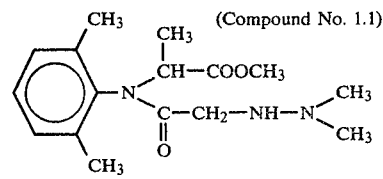

N-(1'-methoxycarbonyl-ethyl)-N-(N',N'-dimethyl-hydrazinoacetyl)-2,6-dimethylaniline 18 g (0.3 mol) of N,N-dimethylhydrazine is added at room temperature to 28.4 g (0.1 mol) of N-(1'-methoxycarbonyl-ethyl)-N-chloroacetyl-2,6-dimethylaniline in 150 ml of toluene. The reaction mixture is then stirred at 50°-60° C. for 96 hours. After cooling to room temperature, there is added about 100 ml of 1 N sodium hydroxide solution, and the organic phase is separated. The aqueous solution is extracted with toluene, the toluene solutions are combined, and washed once with water. After being dried with sodium sulfate, the toluene solution is concentrated in a water-jet vacuum. The brown oil remaining is taken up in petroleum ether, whereupon the product crystallises and is filtered off. The petroleum ether solution is concentrated by evaporation to leave 7.7 g of product in the form of brown oil; $n_D^{21} = 1.5272$.

Also the following compounds are produced in this manner or by one of the methods mentioned in the foregoing.

Table

Compounds of the formula I ($R_2$ in the 6-position)

| Comp. No. | $R_1$ | $R_2$ | $R_3$ | $R_4$ | $R_5$ | $R_6$ | Physical data |
|---|---|---|---|---|---|---|---|
| 1 | $CH_3$ | $CH_3$ | H | H | $CH_3$ | $CH_3$ | $n_D^{21}$ 1,5272 |
| 2 | $CH_3$ | $CH_3$ | 3-$CH_3$ | H | $CH_3$ | $CH_3$ | $n_D^{21}$ 1,6903 |
| 3 | $CH_3$ | $CH_3$ | 3-$CH_3$ | 5-$CH_3$ | $CH_3$ | $CH_3$ | m.p. 85°–91° |
| 4 | $CH_3$ | $CH_3$ | 3-Cl | H | $CH_3$ | $CH_3$ | viscous oil |
| 5 | $CH_3$ | $CH_3$ | 4-Cl | H | $CH_3$ | $CH_3$ | oil |
| 6 | $CH_3$ | Cl | H | H | $CH_3$ | $CH_3$ | oil |
| 7 | $CH_3$ | —$OCH_3$ | H | H | $CH_3$ | $CH_3$ | $n_D^{24}$ 1,5301 |
| 8 | $CH_3$ | $CH_3$ | 3-Br | H | $CH_3$ | $CH_3$ | |
| 9 | $CH_3$ | $C_2H_5$ | H | H | $CH_3$ | $CH_3$ | |
| 10 | $CH_3$ | $CH_3$ | H | H | $CH_3$ | $C_2H_5$ | |
| 11 | $CH_3$ | $CH_3$ | H | H | $C_2H_5$ | $C_2H_5$ | |
| 12 | $CH_3$ | $CH_3$ | H | H | $CH_3$ | $C_3H_7(n)$ | |
| 13 | $CH_3$ | $CH_3$ | H | H | $C_6H_5$ | H | $n_D^{32}$ 1,5580 |
| 14 | $CH_3$ | $CH_3$ | 3-$CH_3$ | H | $C_6H_5$ | H | $n_D^{21}$ 1,5603 |
| 15 | $CH_3$ | $CH_3$ | 3-$CH_3$ | 5-$CH_3$ | $C_6H_5$ | H | $n_D^{21}$ 1,5620 |
| 16 | $CH_3$ | $CH_3$ | H | H | $CH_3O-\langle \bigcirc \rangle-$ | H | |
| 17 | $CH_3$ | $CH_3$ | H | H | $C_6H_5-CH_2-$ | H | |
| 18 | $CH_3$ | $CH_3$ | H | H | $C_3H_7(n)$ | H | oil |
| 19 | $CH_3$ | $CH_3$ | 3-$CH_3$ | H | $C_4H_9(n)$ | H | oil |
| 20 | $CH_3$ | $CH_3$ | H | H | $C_5H_{11}(n)$ | H | |
| 21 | $CH_3$ | $CH_3$ | H | H | $CH_3$ | H | $n_D^{21}$ 1,5293 |
| 22 | $CH_3$ | $CH_3$ | 3-$CH_3$ | H | $CH_3$ | H | |
| 23 | $CH_3$ | $CH_3$ | 3-$CH_3$ | 5-$CH_3$ | $CH_3$ | H | |
| 24 | $CH_3$ | $CH_3$ | H | H | $C_3H_7(iso)$ | H | oil |
| 25 | $CH_3$ | $CH_3$ | H | H | $Cl-\langle \bigcirc \rangle-$ | H | |
| 26 | $CH_3$ | $CH_3$ | H | H | $(CH_3)_3C-$ | H | |

The compounds of the formula I can be used on their own or together with suitable carriers and/or other additives. Suitable carriers and additives can be solid or liquid and they correspond to the substances common in formulation practice, such as natural or regenerated mineral substances, solvents, dispersing agents, wetting agents, adhesives, thickeners, binders and/or fertilisers. Active substances of the formula I can be used in admixture with other pesticidal preparations or other preparations improving plant growth.

The content of active substance in commercial compositions is between 0.1 and 90%.

For application, the compounds of the formula I can be in the following forms (the weight-percentage figures in brackets signify advantageous amounts of active substance):

solid preparations: dusts and scattering agents (up to 10%), granules [coated, impregnated or homogeneous granules] or pellets (1 to 80%);

liquid preparations:
  (a) water-dispersible concentrates of active substance: wettable powders and pastes (25 to 90% in the commercial packing, 0.01 to 15% in ready-for-use solutions); emulsion concentrates and solution concentrates (10 to 50%; 0.01 to 15% in ready-for-use solutions);
  (b) solutions (0.1 to 20%); aerosols.

The active substances of the formula I of the present invention can be formulated for example as follows.

Dust

The following substances are used to produce (a) a 5% dust and (b) a 2% dust:

(a)

5 parts of active substance, and
95 parts of talcum;

(b)

2 parts of active substance,
1 part of highly dispersed silicic acid, and
97 parts of talcum.

The active substances are mixed and ground with the carriers, and in this form they can be applied by dusting.

Granulate

The following substances are used to produce a 5% granulate:
5 parts of active substance,
0.25 part of epichlorohydrin,
0.25 part of cetyl polyglycol ether,
3.50 parts of polyethylene glycol, and
91 parts of kaolin (particle size 0.3–0.8 mm).

The active substance is mixed with epichlorohydrin and dissolved in 6 parts of acetone, and the polyethylene glycol and cetyl polyglycol ether are then added.

The solution obtained is sprayed onto kaolin, and the acetone is subsequently evaporated off in vacuo. A microgranulate of this kind is advantageously used for combating soil fungi.

Wettable powder:

The following constituents are used to produce (a) a 70% wettable powder, (b) a 40% wettable powder, (c) and (d) a 25% wettable powder, and (e) a 10% wettable powder:

(a)

70 parts of active substance,
5 parts of sodium dibutylnaphthylsulfonate,
3 parts of naphthalenesulfonic acid/phenolsulfonic acid/formaldehyde condensate 3:2:1,
10 parts of kaolin, and
12 parts of Champagne chalk;

(b)

40 parts of active substance,
5 parts of sodium lignin sulfonate,
1 part of sodium dibutylnaphthalenesulfonate,
54 parts of silicic acid;

(c)

25 parts of active substance,
4.5 parts of calcium lignin sulfonate,
1.9 parts of Champage chalk/hydroxyethyl cellulose mixture (1:1),
1.5 parts of sodium dibutylnaphthalenesulfonate,
19.5 parts of silicic acid,
19.5 parts of Champagne chalk, and
28.1 parts of kaolin;

(d)

25 parts of active substance,
2.5 parts of isooctylphenoxy-polyoxyethylene-ethanol,
1.7 parts of Champagne chalk/hydroxyethylcellulose mixture (1:1),
8.3 parts of sodium aluminium silicate,
16.5 parts of kieselgur, and
46 parts of kaolin; and (e)

10 parts of active substance,
3 parts of a mixture of the sodium salts of saturated fatty alcohol sulfates,
5 parts of naphthalenesulfonic acid/formaldehyde condensate, and
82 parts of kaolin.

The active substances are intimately mixed in suitable mixers with the additives, and the mixture is then ground in the appropriate mills and rollers. There are obtained wettable powders which have excellent wetting and suspension properties, and which can be diluted with water to give suspensions of the desired concentration, and there are particularly suitable for leaf application.

Emulsifiable concentrate

The following substances are used to produce a 25% emulsifiable concentrate:
25 parts of active substance,
2.5 parts of epoxidised vegetable oil,
10 parts of an alkylarylsulfonate/fatty alcohol polyglycol ether mixture,
5 parts dimethylformamide, and
57.5 parts of xylene.

Emulsions of the desired concentration can be prepared from these concentrates by dilution with water, and they are particularly suitable for leaf application.

EXAMPLE 2

Action against Cercospora personata (=C. arachidicola) on groundnut plants

Three-week-old groundnut plants are sprayed with a spray liquor produced from wettable powder of the active substance (0.02% of active substance). The treated plants are dusted after about 12 hours with a conidiospore suspension of the fungus. The infected plants are then incubated for about 24 hours with 90% relative humidity, and are subsequently transferred to a greenhouse at about 22°. The fungus infection is assessed after 12 days.

In comparison with the untreated control plants, plants which have been treated with active substances of the formula I display only slight fungus infection or virtually no infection at all.

EXAMPLE 3

Action against Phytophthora infestans on tomatoes (Ia) Residual-preventive action Tomato plants of the "Roter Gnom" (red gnome) variety are sprayed after three weeks' cultivation with a liquor containing 0.06% of active substance (prepared from the active substance made up as a wettable powder); the applied coating is allowed to dry, and the plants are then infested with a zoospore suspension of Phytophthora infestans. The plants subsequently remain for 6 days in a controlled-atmosphere chamber at 18° to 20°, with a high atmospheric humidity being produced by means of an artificial spray. After this length of time, typical leaf spots appear on the infected but untreated control plants. The size and number of these leaf spots are a basis of assessment for the treated plants, and hence also for the respective substance tested.

(Ib) Curative action

Tomato plants of the "Red Gnom" variety are sprayed, after three-weeks' cultivation, with a zoospore suspension of the fungus, and incubated in a chamber at 18° to 20° with saturated atmospheric humidity. The moistening treatment is interrupted after 24 hours; the plants are dried and then sprayed with a liquid containing the active substance formulated as a wettable powder, at a concentration of 0.06%. The applied coating is allowed to dry, and the plants are then returned to the moist-atmosphere chamber for 4 days. The number and size of the typical leaf spots appearing after this time on the control plants are the basis of assessment for evaluating the treated plants.

(II) Preventive-systemic action

The active substance in the form of a wettable powder is applied at a concentration of 0.006% (relative to the volume of soil) to the surface of the soil of three-week-old potted tomato plants of the "Red Gnom" variety. After a period of three days, the underside of the leaves of the plants is sprayed with a zoospore suspension of Phytophthora infestans. The plants are then stored for 5 days in a spray chamber at 18°–20° with a saturated atmosphere. The typical leaf spots appear after this time; on the basis of their number and size, an evaluation is then made of the effectiveness of the substances tested.

In these three tests, the compounds of the formula I exhibit a good leaf-fungicidal action, for example the compounds Nos. 1 to 7, 10, 21, 22, 23 and others (0 to 10% fungus infection). The compounds Nos. 1, 2, 3, 4, 7, 13, 14 and 15 in Tests I and II prevent even at a spray concentration of 0.02% infection occurring. In Test III, the compounds 1, 2, 3, 4, 7, 13 and 14 at a concentration of 0.002% prevent the occurrence of infection.

EXAMPLE 4

Action against Plasmopara viticola (Bert. et Curt.) (Berl. et DeToni) on grape vines Residual-preventive action Grape-vine cuttings of the "Chasselas" variety are grown in a greenhouse. Three plants are sprayed in the 10-leaf stage with a liquor prepared from the active substance formulated as a wettable powder (0.02% of active substance). After drying of the applied coating, the plants are uniformly infested on the underside of the leaves with the spore suspension of the fungus. The plants are subsequently kept for 8 days in a moist chamber. Clear symptoms of infection have appeared on the control plants after this period of time. The number and size of the areas of infection on the treated plants serve as a criterion for the evaluation of the effectiveness of the substances tested. The occurrence of disease is prevented completely with the compounds Nos. 1, 2, 3, 4, 13, 14 and 15.

EXAMPLE 5

Action against Phythium debaryanum on sugar beet (a) Action after soil application The fungus is cultivated on sterile oat grains, and then applied to a soil/sand mixture. The soil infected in this manner is put into flower pots and sown with sugar-beet seeds. Directly after sowing, the test preparations (formulated as wettable powders) are poured as aqueous suspensions over the soil (0.002% of active substance relative to the volume of soil). The pots are then kept for 2–3 weeks at 20°–24° in a greenhouse. The soil is maintained uniformly moist during this period by a light spraying with water. In the assessment of the test results, an observation is made of the emergence of the sugar-beet plants and also of the proportion of healthy and diseased plants, respectively.

(b) Action after dressing application

The fungus is cultivated on sterile oat grains and then applied to a soil/sand mixture. The soil infected in this manner is placed into flower pots and sown with sugar-beet seeds which have been dressed with the test preparations formulated as dressing powders (0.1% of active substance relative to the weight of seed). The sown pots are kept for 2–3 weeks at 20°–24° in a greenhouse. The soil during this period is maintained uniformly moist by a light spraying with water. In the assessment of the test results, the emergence of the sugar-beet plants is observed and the proportion of healthy and diseased plants, respectively, is determined.

After the treatment with the active substances of the formula I, more than 80% of the sugar-beet plants emerge both under the test conditions (a) and (b), and the plants have a healthy appearance. Where treatment is carried out with the active substances Nos. 1 to 4, inclusive, and 14, more than 90% of the plants emerge in a healthy condition.

What is claimed is:

1. A compound of the formula, and salts thereof which are tolerated by plants,

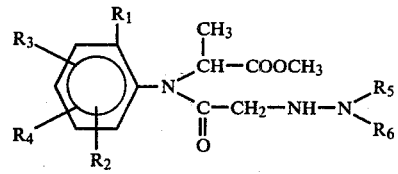

wherein
$R_1$ is $C_1$–$C_4$ alkyl, $C_1$–$C_4$ alkoxy or halogen,
$R_2$ is $C_1$–$C_3$ alkyl, $C_1$–$C_4$ alkoxy or halogen,
$R_3$ is hydrogen, $C_1$–$C_3$ alkyl or halogen,
$R_4$ is hydrogen or methyl, with the total number of C atoms of the substituents $R_1$, $R_2$, $R_3$ and $R_4$ in the phenyl ring not exceeding 6,
$R_5$ is $C_1$–$C_5$ alkyl which is unsubstituted or substituted by halogen, or it is phenyl which is unsubstituted or substituted by methyl, nitro and/or halogen, or it is the benzyl group, and
$R_6$ is hydrogen or $C_1$–$C_5$ alkyl.

2. A compound of the formula I according to claim 1, wherein $R_1$ is methyl, $R_2$ is in the ortho position with respect to the amino group and is methyl, methoxy or chlorine, $R_3$ is hydrogen, methyl or chlorine, and $R_4$ is hydrogen or methyl.

3. N-(1'-Methoxycarbonyl-ethyl)-N-(N',N'-dimethylhydrazinoacetyl)-2,6-dimethylaniline according to claim 1.

4. N-(1'-Methoxycarbonyl-ethyl)-N-(N',N'-dimethylhydrazinoacetyl)-2,6-dimethyl-3-chloroaniline according to claim 1.

5. N-(1'-Methoxycarbonyl-ethyl)-N-(N'-phenylhydrazinoacetyl)-2,6-dimethylaniline of the formula

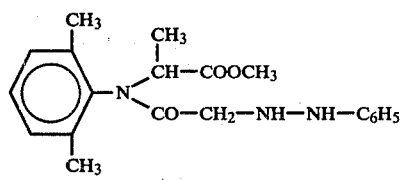

according to claim 1.

6. N-(1'-Methoxycarbonyl-ethyl)-N-(N'-phenylhydrazinoacetyl)-2,3,6-trimethylaniline according to claim 1.

7. A composition for combating fungi, which composition contains, as at least one active ingredient, an effective amount of a compound of the formula, or one of its salts tolerated by plants.

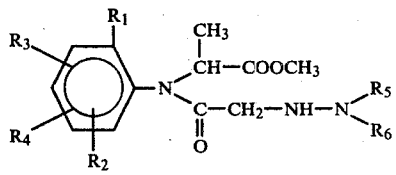

wherein
$R_1$ is $C_1$–$C_4$ alkyl, $C_1$–$C_4$ alkoxy or halogen,
$R_2$ is $C_1$–$C_3$ alkyl, $C_1$–$C_4$ alkoxy or halogen, $R_3$ is hydrogen, $C_1$–$C_3$ alkyl or halogen, $R_4$ is hydrogen or methyl, with the total number of C atoms of the substituents $R_1$, $R_2$, $R_3$ and $R_4$ in the phenyl ring not exceeding 6, $R_5$ is $C_1$–$C_5$ alkyl which is unsubstituted or substituted by halogen, or it is phenyl which is unsubstituted or substituted by methyl, nitro and/or halogen, or it is the benzyl group, and $R_6$ is hydrogen or $C_1$–$C_5$ alkyl, together with a suitable carrier therefor.

8. A composition according to claim 7, which contains as active ingredient a compound of the formula I wherein $R_1$ is methyl, $R_2$ is in the ortho-position with respect to the amino group and is methyl, methoxy or chlorine, $R_3$ is hydrogen, methyl or chlorine, and $R_4$ is hydrogen or methyl.

9. A composition according to claim 7, which contains as active ingredient one of the following compounds: N-(1'-methoxycarbonyl-ethyl)-N-(N',N'-dimethylhydrazinoacetyl)-2,6-dimethylaniline, N-(1'-methoxycarbonyl-ethyl)-N-(N',N'-dimethylhydrazinoacetyl)-2,6-dimethyl-3-chloroaniline, N-(1'-methoxycarbonyl-ethyl)-N-(N'-phenylhydrazinoacetyl)-2,6-dimethylaniline and N-(1'-methoxycarbonyl-ethyl)-N-(N'-phenylhydrazinoacetyl)-2,3,6-trimethylaniline.

10. A process for combating phytopathogenic fungi or preventing plants from their attack, which process involves the application of an effective amount of a compound of claim 1.

* * * * *